United States Patent
Zilch et al.

(10) Patent No.: US 6,372,725 B1
(45) Date of Patent: Apr. 16, 2002

(54) SPECIFIC LIPID CONJUGATES TO NUCLEOSIDE DIPHOSPHATES AND THEIR USE AS DRUGS

(76) Inventors: Harald Zilch, Alsenweg 24, D-68305 Mannheim; Dieter Herrmann, An der Neckarspitze 13, D-69115 Heidelberg, both of (DE)

( * ) Notice: Subject to any disclaimer, the term of this patent is extended or adjusted under 35 U.S.C. 154(b) by 0 days.

(21) Appl. No.: 09/204,497

(22) Filed: Dec. 4, 1998

Related U.S. Application Data

(63) Continuation of application No. 08/875,928, filed as application No. PCT/EP96/00653 on Feb. 15, 1996, now abandoned.

Foreign Application Priority Data

Feb. 16, 1995 (DE) .......................... 195 05 168

(51) Int. Cl.$^7$ .......................... A61K 31/70; C07H 19/04

(52) U.S. Cl. .............................. 514/48; 514/43; 514/45; 514/49; 536/26.1; 536/26.7; 536/26.8; 536/26.9; 536/26.5; 536/26.23

(58) Field of Search ................... 536/26.1, 26.7, 536/26.8, 26.9, 26.23, 26.5, 26.71; 424/450; 514/42, 43, 45, 48, 49

(56) References Cited

U.S. PATENT DOCUMENTS 5,223,263 A * 6/1993 Hostetler ............... 424/450
5,563,257 A * 10/1996 Zilch et al. ............ 536/26.14

* cited by examiner

*Primary Examiner*—Gary Geist
*Assistant Examiner*—Howard V. Owens, Jr.
(74) *Attorney, Agent, or Firm*—Arent, Fox, Kintner, Plotkin & Kahn

(57) ABSTRACT

The present invention concerns new phospholipid derivatives of nucleosides of the general formula (I) in which $R^1$ represents a straight-chained or branched, saturated or unsaturated aliphatic residue with 9–14 carbon atoms which can optionally be substituted once or several times; $R^2$ can represent a straight-chained or branched, saturated or unsaturated aliphatic residue with 8–12 carbon atoms which can optionally be substituted once or several times; m is 2 or 3; A can represent a methylene group or an oxygen; Nuc can be a nucleoside or a residue derived from a nucleoside derivative; and tautomers thereof and their physiologically tolerated salts of inorganic and organic acids and bases as well as pharmaceutical preparations containing these compounds.

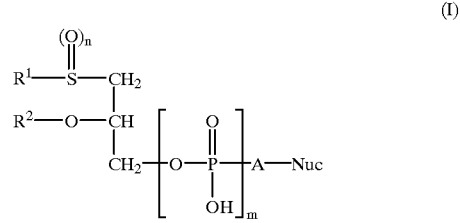

(I)

6 Claims, No Drawings

SPECIFIC LIPID CONJUGATES TO NUCLEOSIDE DIPHOSPHATES AND THEIR USE AS DRUGS

This application is a continuation of application Ser. No. 08/875,928, filed Aug. 13, 1997, now abandoned, which is the U.S. national stage of PCT/EP96/00653, filed Feb. 15, 1996.

The present invention concerns new phospholipid derivatives of nucleosides of the general formula I

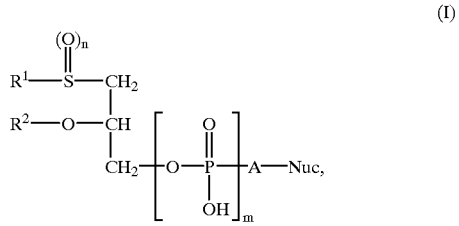

in which
R$^1$ denotes a straight-chained or branched, saturated or unsaturated aliphatic residue with 9–14 carbon atoms which can optionally be substituted once or several times by phenyl, halogen, $C_1$–$C_6$ alkoxy, $C_1$–$C_6$ alkyl-mercapto, $C_1$–$C_6$ alkoxycarbonyl, $C_1$–$C_6$ alkylsulfinyl or $C_1$–$C_6$ alkylsulfonyl groups, R$^2$ represents a straight-chained or branched, saturated or unsaturated aliphatic residue with 8–12 carbon atoms which can be substituted once or several times by phenyl, halogen, $C_1$–$C_6$ alkoxy, $C_1$–$C_6$ alkyl-mercapto, $C_1$–$C_6$ alkoxycarbonyl or $C_1$–$C_6$ alkylsulfonyl groups, m equals 2 or 3, A can represents a methylene group or an oxygen, Nuc can be a nucleoside or a residue derived from a nucleoside derivative, as well as tautomers thereof and their physiologically tolerated salts of inorganic and organic acids and bases, and pharmaceutical preparations containing these compounds.

Since the compounds of the general formula I contain asymmetric carbon atoms, the present invention also concerns all optically active forms and racemic mixtures of these compounds.

Numerous nucleoside diphosphate diacylglycerols and their production are described in the literature. The synthesis of corresponding derivatives of AZT, DDC and d2T is described in Biochim. Biophys. Acta 1165, 45 (1992) and J. Lipid Res. 33, 1211 (1992).

Biochem. Biophys. Acta 1084, 307 (1991) and 1086, 99 (1991) shows the release of the nucleoside monophosphate by mitochondrial enzyme activity from rat liver.

The protein-induced intermembrane transfer of antiviral derivatives as well as their synthesis is described by Biochemistry 31, 5912 (1992) and J. Biol. Chem. 265, 6112 (1990).

The antitumoural action of ara-C diphosphate derivatives with ether and thioether lipids in the SN1 positions is described in LIPIDS 26, 1437 (1991), Drugs of the Future 15, 245 (1990), Exp. Hematol. 17, 364 (1989), J. Med. Chem. 33, 1380 (1990) and Cancer Res. 50, 4401 (1990).

EP 0 376 518 demonstrates the antineoplastic properties of 2'-deoxy-2',2'-difluoronucleoside derivatives and J. Med. Chem. 25, 1322 (1982) and 31, 1793 (1988) give information on the synthesis and antitumoural action of ara-C-5'-diphosphate diacylglycerols.

The applications DD-290-197 and EP 0 432 183 describe the synthesis of cytidine-5'-diphosphate-1-0-alkyl-glycerol with antitumoural action and EP 0 355 016 describes the synthesis of corresponding diphosphate glycerols.

The production of ara-C-5'-diphosphate-1-O-octadecyl-2-O-palmitoylglycerol is described in DE 35 43 346 and d2T-5'-diphosphate-dimyristoylglycerol with its antiviral action is known from Antimicrob. Agent. Chemother. 36, 2025 (1992).

Some of the derivatives described in this application are included in the patent document WO 91/19726 (PCT/US91/04289) and U.S. Pat. No. 4,622,392, but their description is very speculative and they do not contain any concrete details on the production of the compounds described in this application. Furthermore the compounds described in this application surprisingly have advantageous properties with regard to their pharmacological action which distinguishes them from the compounds described in the above-mentioned patent documents.

The compounds of the present invention are new and have valuable pharmacological properties. In particular they are suitable for the therapy and prophylaxis of infections which are caused by DNA viruses such as e.g. the herpes simplex virus, the cytomegaly virus, papilloma virus, the Varicella-Zoster virus or Epstein-Barr virus or RNA viruses such as Toga viruses or in particular retroviruses such as the oncoviruses HTLV-I and II as well as the lentiviruses visna and human immune deficiency virus HIV-1 and 2.

The compounds of formula I appear to be particularly suitable for the treatment of the clinical manifestations of retroviral HIV infection in humans such as persistent generalized lymphoadenopathy (PGL), the advanced stage of the AIDS-related complex and the full clinical picture of AIDS.

In addition the compounds of formula I are suitable for the therapy and prophylaxis of malignant tumours such as malignomas and neoplasias (carcinomas, sarcomas, leukaemia etc.) in tumour therapy as well as for the inhibition of oncogenic viruses.

In general the compound of formula I are then of interest when the coupled nucleoside (Nuc) has for example a cytotoxic, antitumoural, antiviral, anti-retroviral, immunosuppressive or immunostimulating action and cannot be used or only to a limited extent as a pharmaceutical agent because of side-effects, a too narrow therapeutic range or organ toxicities.

In comparison to the nucleosides that have been previously used for treatment, the compounds according to the invention have a low toxicity. They therefore have the advantage that pharmaceutical preparations that contain these compounds can be administered continuously over a long time period and it is possible to avoid discontinuation of the preparation or an intermittent administration as a result of undesired side-effects.

The compounds of the present invention and their pharmaceutical preparation can also be used in combination with other drugs for the treatment and prophylaxis of various diseases. Examples of these preparations containing further drugs are those which can be used for the treatment and prophylaxis of HIV infections and illnesses accompanying this disease or drugs with a cytostatic/cytotoxic or immunosuppressive/-stimulating action.

The conjugates of formula I have decisive advantages in comparison to the non-conjugated active substance.

The carrier that is specifically covalently bound to the active substance improves the bioavailability of poorly resorbed active substances, improves the tolerance of potentially toxic active molecules and the retention time of rapidly eliminated or metabolized drugs.

The carrier part with its lecithin-like structure which is essential for the claimed effect improves the penetration/membrane permeability of the active substance and has a depot effect in many cases.

The gastrointestinal tolerance of the claimed lipid conjugates is in many cases better than that of the pure active substances.

The heteroatoms in the residues —S(O)n—$R^1$ and —O—$R^2$ in the lipid part cannot be replaced by the carboxylic acid esters known from lecithin since otherwise there would already be a hydrolytic cleavage in the serum to form the corresponding lysolecithin derivatives/glycerol esters with a corresponding more rapid elimination of the active substance.

The thioether/ether lipids of this application do not exhibit this cleavage in the serum of humans.

Also in the resorption the lipid conjugate exhibits a better penetration through membrane structures and thus a better surmounting of the resorption barriers and for example the blood-brain barrier by a facilitated diffusion or possibly active transport.

The improved binding of the conjugate to plasma and tissue proteins also improves the in vivo distribution. The conjugate is primarily oxidized from the thioether to the sulfoxide by normal biotransformation which, however, is not a disadvantage due to the almost equipotent effect of the sulfoxide in comparison to the thioether.

The slow release of the active substance from the conjugate ensures a low but constant level of the active substance over a relatively long time period and avoids a toxic side-effect.

The released active substance can for example have a cytotoxic, antitumoural, antiviral, antiretroviral, immunosuppressive or immunostimulating action.

Alkali, alkaline earth and ammonium salts of the phosphate group come primarily into consideration as possible salts of compounds of the general formula I. Lithium, sodium and potassium salts are preferred as alkali salts. Magnesium and calcium salts come into special consideration as alkaline earth salts. Ammonium salts are understood as salts according to the invention which contain the ammonium ion which can be substituted up to four times by alkyl residues with 1–4 carbon atoms and/or aralkyl residues, preferably benzyl residues. In this case the substituents can be the same or different.

The compounds of the general formula I can contain basic groups, in particular amino groups which can be converted with suitable acids into acid addition salts. Hydrochloric acid, hydrobromic acid, sulfuric acid, phosphoric acid, fumaric acid, succinic acid, tartaric acid, citric acid, lactic acid, maleic acid or methane-sulfonic acid come for example into consideration as acids for this.

An aliphatic residue in the definition of $R^1$ and $R^2$ in particular denotes an alkyl, alkenyl or alkinyl group.

In the general formula I $R^1$ preferably denotes a straight-chained $C_{10}$–$C_{14}$ alkyl group which can additionally be substituted by a $C_1$–$C_6$ alkoxy or a $C_1$–$C_6$ alkylmercapto group. $R^1$ in particular denotes a decyl, undecyl, dodecyl, tridecyl or tetradecyl group. A methoxy, ethoxy, butoxy and hexyloxy group come preferably into consideration as $C_1$–$C_6$ alkylmercapto substituents for $R^1$. In the case that $R^1$ is substituted by a $C_1$–$C_6$ alkylmercapto residue this is in particular understood as a methylmercapto, ethylmercapto, propyl-mercapto, butylmercapto and hexylmercapto residue.

$R^2$ preferably denotes a straight-chained $C_{10}$–$C_{12}$ alkyl group which can additionally be substituted by a $C_1$–$C_6$ alkoxy group or a $C_1$–$C_6$ alkylmercapto group. $R^2$ in particular represents a decyl, undecyl or dodecyl group. A methoxy, ethoxy, propoxy, butoxy and a hexyloxy group come preferably into consideration as $C_1$–$C_6$ alkoxy substituents for $R^2$.

In the case that $R^2$ is substituted by a $C_1$–$C_6$ alkylmercapto residue this is in particular understood as a methylmercapto, ethylmercapto, butylmercapto and hexylmercapto residue.

The residue Nuc denotes a nucleoside derivative which is bound via the 5' position to the pyrophosphoric acid of the lipophilic part of formula I. The following residues come for example into consideration as nucleosides or nucleoside analogues:

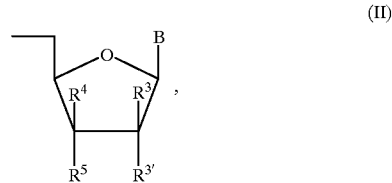

(II)

in which $R^3$, $R^{3'}$ can denote oxygen, halogen or a hydroxy group, $R^4$, $R^5$ can in each case denote hydrogen or one of the residues $R^4$ and $R^5$ denote a hydroxy, a cyano or an azido group and $R^3$ and $R^4$ can in addition represent a further bond between C–2' and C–3', B denotes one of the following compounds:

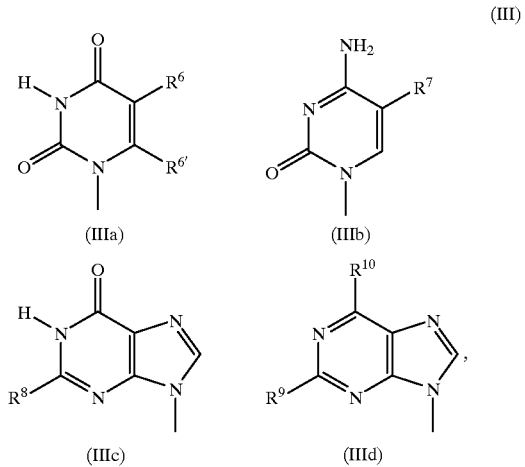

wherein $R^6$ can be oxygen, an alkyl chain with 1–6 carbon atoms, a $C_2$–$C_6$ alkenyl residue which is optionally substituted by halogen, a $C_2$–$C_6$ alkinyl residue or halogen.

$R^{6'}$ can be hydrogen or a benzyl or phenylthio residue, $R^7$ can be hydrogen, an alkyl chain with 1–6 carbon atoms, a $C_2$–$C_6$ alkenyl residue which optionally is substituted by halogen, a $C_2$–$C_6$ alkinyl residue or halogen, $R^8$ can be hydrogen, an alkyl chain with 1–6 carbon atoms, halogen or a hydroxy or amino group, $R^9$ can be hydrogen, halogen or an amino group and $R^{10}$ can be hydrogen, halogen, $C_1$–$C_6$ alkoxy, $C_1$–$C_6$ alkyl-mercapto, mercapto or an amino group which can be monosubstituted or disubstituted by $C_1$–$C_6$ alkyl, $C_1$–$C_6$ alkoxy, hydroxy-$C_2$-$C_6$-alkyl and/or $C_3$–$C_6$ cycloalkyl, aryl, hetaryl, aralkyl or hetarylalkyl groups which optionally can be substituted in the aryl or hetaryl residue by one or several hydroxy, methoxy or alkyl groups or halogen, or allyl which can optionally be substituted by mono or dialkyl or alkoxy groups.

Nuc can also be a carbocyclic residue of the type

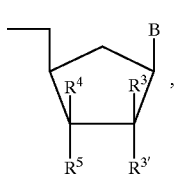

(IV)

or a cyclobutane, oxetanozine residue or a residue derived from a seco-nucleoside derivatives of the type —$CH_2$—$CH_2$—O—$CH_2$—B or —$CH_2$—O—$CH_2$—CH2—B such as for example described in WO 90/09998 or WO 90/09999 in which $R^3$, $R^{3'}$, $R^4$, $R^5$ and B have the meanings stated above.

Such nucleoside or nucleoside analogues come in particular into consideration for Nuc which can be derived from the known active compounds such as e.g. Carbovir, HEPT, Ganciclovir, pentostatin, ara-C, ara-A, ara-G and others.

$R^4$ and $R^5$ in the nucleosides Nuc of formula II preferably in each case denote hydrogen or one of the two residues is preferably cyano, azido or halogen such as fluorine, chlorine, bromine or iodine, hydroxy also being preferred for $R^5$.

One of the two residues $R^3$ or $R^{3'}$ preferably equals hydroxy when the other residue is hydrogen. $R^3$ and $R^{3'}$ can simultaneously also preferably be hydrogen or halogen such as for example fluorine.

Compounds are particularly preferred in which $R^3$ and $R^4$ represent a hydrogen atom and $R^5$ is hydroxy, cyano, azido or fluorine or $R^5$ is hydrogen and $R^3/R^4$ represent a further bond between C–2' and C–3' as well as arabino and ribo-furanosides.

In the bases B of formula III $R^6$ and $R^7$ preferably denote a hydrogen atom, a methyl, ethyl, propyl or butyl residue, an ethinyl, propinyl, vinyl or propenyl residue or a halogen atom such as fluorine, chlorine, bromine or iodine. A hydrogen atom, a methyl or ethyl residue and a fluorine, chlorine or bromine atom are especially preferred for $R^6$ or $R^7$.

The residue $R^8$ is preferably a hydrogen atom, a methyl, ethyl, propyl or butyl residue, an amino group or a halogen atom such as fluorine, chlorine, bromine or iodine, preferably chlorine or bromine.

$R^{10}$ preferably denotes a hydrogen, fluorine, chlorine or bromine atom, a mercapto residue, a $C_1$–$C_6$ alkoxy group in particular a methoxy-ethoxy, propoxy, butoxy or hexyloxy group, a $C_1$–$C_6$ alkylmercapto group in particular a methylmercapto, ethylmercapto, butylmercapto or hexylmercapto group or an amino group which can be monosubstituted or disubstituted by a $C_1$–$C_6$ alkyl group such as e.g. a methyl, ethyl, butyl or hexyl group which can optionally be substituted by a hydroxy-$C_2$–$C_6$-alkyl group such as e.g. a hydroxyethyl, hydroxypropyl, hydroxybutyl or hydroxyhexyl group, by a $C_3$–$C_6$ cycloalkyl residue such as e.g. a cyclopropyl, cyclopentyl or cyclohexyl residue, by aryl preferably phenyl, by an aralkyl residue such as in particular benzyl which can optionally be substituted by an one or several hydroxy or methoxy groups, by $C_1$–$C_6$ alkyl groups such as e.g. a methyl, ethyl, propyl, butyl or hexyl group or by halogen atoms such as fluorine, chlorine or bromine. The amino group can also be substituted by a heterarylalkyl or hetaryl residue such as in particular e.g. a thienyl, a furyl or pyridyl residue. The heterarylalkyl residue is preferably understood as a thienylmethyl, furylmethyl or pyridylmethyl residue.

m preferably equals 2 and A preferably represents an oxygen atom.

Preferred coupled nucleosides in the claimed liponucleotides of the general formula I are:

2',3'-dideoxy-3'-azidouridine

2',3'-dideoxyinosine

2',3'-dideoxyguanosine

2',3'-dideoxycytidine

2',3'-dideoxyadenosine

2',3'-deoxythymidine

2',3'-dideoxy-2'-3'-didehydro-$N^6$-(o-methylbenzyl)-adenosine

2',3'-dideoxy-2'-3'-didehydro-$N^6$-(2-methylpropyl)-adenosine

2',3'-dideoxy-3'-azidoguanosine

3'-deoxy-3'-azido-thymidine

2',3'-dideoxy-3'-fluoro-5-chlorouridine

3'-deoxy-3'-fluorothymidine

2',3'-dideoxy-3'-fluoroadenosine

2',3'-dideoxy-3'-fluoro-2,6-diaminopurine-riboside

2',3'-dideoxy-2'-3'-didehydrocytidine

3'-deoxy-2'-3'-didehydrothymidine 5-fluorouridine 6-mercaptopurine-9-β-D-ribofuranoside Acyclovir Ganciclovir adenine-9-β-D-arabinofuranoside 2-chloro-2'-deoxyadenosine 3-(2-deoxy-β-D-erythro-pentofuranosyl) -3,6,7,8-tetrahydro-imidazo[4,5-d][1,3] diazepin-8-ol cytosine-9-β-D-arabinofuranoside guanine-9-β-D-arabinofuranoside hypoxanthine-9-β-D-arabinofuranoside 2'-deoxy-2-fluoroadenosine 2-fluoroadenine-9-β-D-arabinofuranoside 2-fluoroadenosine 2-amino-6-mercaptopurine-9-β-D-ribofuranoside 6-methylmercaptopurine-9-β-D-ribofuranoside 3'-deoxy-5-fluorouridine 2-chloroadenosine 3'-deoxy-3'-fluoroadenosine 3'-deoxy-3'-fluoroguanosine 1-(β-D-arabinofuranosyl)-5-ethinyluracil 1-(β-D-arabinofuranosyl)-5-prop-1-inyluracil 1-(β-D-arabinofuranosyl)-5-prop-2-inyluracil The compounds of the general formula I can be produced by known and published processes in which e.g. a compound of the general formula V

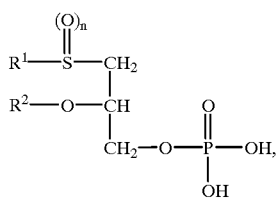

in which $R^1$, $R^2$ and n have the stated meanings is reacted as a morpholidate in the presence of a tertiary nitrogen base e.g. puridine or lutidine in an inert solvent such as e.g. toluene or directly in pyridine with a compound of the general formula VI

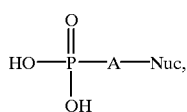

in which Nuc has the meaning stated above and preferably denotes a compound of formula VIa

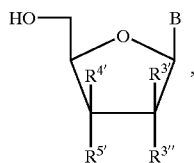

in which $R^{3'}$, $R^{3'''}$ and $R^{5'}$ are hydrogen or a hydroxy group protected by an oxygen protecting group familiar to a person skilled in the art and $R^{4'}$, $R^{5'}$ and $R^{3'''}$ each represent hydrogen, halogen, an azido, cyano or one of the residues $R^{4'}$ and $R^{5'}$ denotes a hydroxy group protected by an oxygen protecting group known to a person skilled in the art or $R^{3'}$ and $R^{4'}$ represent a further bond and B has the stated meanings and, after hydrolysis is completed, the oxygen protecting groups are cleaved off according to common processes in nucleoside chemistry as described for example in J. Lipid Res. 33, 1211 (1992).

Alternatively the morpholidate of the compound of the general formula VI can also be reacted with a phosphate of formula V.

The production of compounds of the general formula V is described in DE 39 29 217 and WO 91/05558.

Compounds similar to the general formula I are described in EP-A-0350287. Here the corresponding 1,2-diesters of glycerol are described.

The pharmaceutical preparations containing compounds of formula I for the treatment of viral infections can be administered enterally or parenterally in a liquid or solid form. For this the usual forms of administration come into consideration such as for example tablets, capsules, dragees, syrups, solutions or suspensions. Water is preferably used as the injection medium which contains the usual additives for injection solutions such as stabilizers, solubilizers and buffers. Such additives are for example tartrate and citrate buffer, ethanol, complexing agents such as ethylenediaminotetraacetic acid and non-toxic salts thereof, high molecular polymers such as liquid polyethylene oxide to regulate viscosity. Liquid carriers for injection solutions have to be sterile and are preferably filled into ampoules.

Solid carriers are for example starch, lactose, mannitol, methylcellulose, talcum, highly dispersed silicic acids, higher molecular fatty acids such as stearic acid, gelatin, agar-agar, calcium phosphate, magnesium stearate, animal and plant fats, solid high molecular polymers such as polyethylene glycols etc. Preparations suitable for oral application can if desired contain flavourings or sweeteners.

The dosage can depend on various factors such as manner of application, species, age or individual state of health. The compounds according to the invention are usually administered in amounts of 0.1–100 mg preferably 0.2–80 mg per day and per kg body weight. The daily dose is preferably administered in 2–5 applications, 1–2 tablets with an active content of 0.5–500 mg being administered at each application. The tablets can also be retarded by which means the number of administrations is reduced to 1–3 per day. The content of active substance of the retarded tablets can be 2–1000 mg. The active substance can also be administered by continuous infusion in which case amounts of 5–1000 mg per day are usually adequate.

The following compounds of formula I come into consideration within the sense of the present invention in addition to the compounds mentioned in the examples and by combination of all meanings of the substituents mentioned in the claims:

(2',3'-dideoxy-3'-fluoro-5-chlorouridine)-5'-diphosphoric acid-(3-dodecylmercapto-2-decyloxy)-1-propyl ester (3'-deoxy-3'-azido-thymidine)-5'-diphosphoric acid-(3-dodecylsulfinyl-2-decyloxy)-1-propyl ester (3'-deoxy-3'-azido-thymidine)-5'-diphosphoric acid-(3-dodecylsulfonyl-2-decyloxy)-1-propyl ester (2',3'-dideoxycytidine)-5'-diphosphoric acid-(3-dodecylmercapto-2-decyloxy)-1-propyl ester (2',3'-dideoxyinosine)-5'-diphosphoric acid-(3-dodecylmercapto-2-decyloxy)-1-propyl ester (5-fluorouridine)-5'-diphosphoric acid-(3-dodecyloxy-2-decyloxy)-1-propyl ester (6-mercaptopurine-9-β-D-ribofuranoside)-5'-diphosphoric acid-(3-dodecylmercapto-2-decyloxy)-1-propyl ester (2-chloro-2'-deoxyadenosine)-5'-diphosphoric acid-(3-dodecylmercapto-2-decylmercapto)-1-propyl ester (3'-deoxy-2',3'-didehydrothymidine)-5'-diphosphoric acid-(3-dodecylmercapto-2-decyloxy)-1-propyl ester (3'-deoxy-3'-fluorothymidine)-5'-diphosphoric acid-(3-dodecylsulfinyl-2-decyloxy)-1-propyl ester (2-fluoroadenine-9-β-D-arabinofuranoside)-5'-diphosphoric acid-(3-dodecylmercapto-2-decyloxy)-1-propyl ester (2-fluoroadenosine)-5'-diphosphoric acid-(3-dodecylmercapto-2-decyloxy)-1-propyl ester (2-amino-6-mercaptopurine-9-β-D-ribofuranoside)-5'-diphosphoric acid-(3-dodecylmercapto-2-decyloxy)-1-propyl ester (2-chloroadenosine)-5'-diphosphoric acid-(3-dodecylmercapto-2-decyloxy)-1-propyl ester (cytosine-1-β-D-arabinofuranoside)-5'-diphosphoric acid-(3-decylmercapto-2-dodecyloxy)-1-propyl ester (2',3'-dideoxy-2-fluoroadenosine)-5'-diphosphoric acid-(3-undecyloxy-2-dodecyloxy)-1-propyl ester (adenine-9-β-D-arabinofuranoside)-5'-diphosphoric acid-(3-decylsulfonyl-2-dodecyloxy)-1-propyl ester (guanine-9-β-D-arabinofuranoside)-5'-diphosphoric acid-(3-decylmercapto-2-decyloxy)-1-propyl ester

[3-(2-deoxy-β-D-erythro-pentofuranosyl)-3,6,7,8-tetrahydroimidazole[4,5-d][1,3]diazepin-8-ol]-5'-diphosphoric acid-(3-dodecylmercapto-2-dodecyloxy)-1-propyl ester (5-fluorouridine)-5'-diphosphoric acid-(3-undecylmercapto-2-undecyloxy)-1-propyl ester (2-chloro-2'-deoxyadenosine)-5'-diphosporic acid-(3-undecylmercapto-2-undecyloxy)-1-propyl ester (6-mercaptouridine-9-β-D-ribofuranoside)-5'-diphosphoric acid-(3-tridecylmercapto-2-decyloxy)-1-propyl ester (3'-deoxy-3'-fluoroadenosine)-5'-diphosphoric acid-(3-dodecylmercapto-2-nonyloxy)-1-propyl ester

EXAMPLE 1

(3'-azido-3'-deoxythymidine)-5'-diphosphoric acid-(3-dodecylmercapto-2-decyloxy)-1-propyl ester The said compound is produced analogously to J. Lipid Res. 33, 1211 (1992) by the dropwise addition of a solution of 9.93 g (20 mmol) phosphoric acid mono(3-dodecylmercapto-2-decyloxy)-1-propyl ester in 250 ml $CH_2Cl_2$ while stirring at room temperature to 7.0 ml (80 mmol) morpholine in 300 ml t-butanol/1.5 ml water and heating it to reflux. A solution of 16.5 g (80 mmol) DCC in 400 ml t-butanol is then added over 2 hours, heated for a further 6 hours under reflux and evaporated after cooling in a rotary evaporator. The residue is suspended in 800 ml water and extracted three times with 300 ml t-butylmethyl ether. The combined organic phases are evaporated, dry distilled several times with pyridine and the residue is used without further purification in the following reaction.

AZT monophosphate is obtained by reaction of 5.35 g (20 mmol) AZT with $POCl_3$ in the presence of proton sponge in trimethyl phosphate, hydrolysis with 1 M triethylammonium bicarbonate solution, evaporating to dryness and chromatography of the residue on RP 18 with $MeOH/H_2O$ 5/1 as the eluant.

The crude morpholidate and the AZT monophosphate are each dissolved in 200 ml pyridine, the solutions are combined and evaporated to dryness. The residue is then dissolved in 400 ml absolute pyridine and stirred for 20 h at 30° C. under a nitrogen atmosphere.

After removing the solvent and stirring out with t-butylmethyl ether, the evaporation residue is purified by preparative column chromatography on RP 18 using methanol/0.01 M acetate buffer 87/13 pH 5 as the eluant. Yield 8.8 g (59% of theory). Paste $R_f$=0.45 (methanol/$H_2O$ 85/15), RP 18 TLC plates Merck 15685; $R_f$=0.32 (dichloromethane/methanol/water 65/25/4 and $R_f$=0.13 (i-propanol/butyl acetate/glacial acetic acid/water 5/3/1/1) on TLC plates Merck 5719. The compound can be filled after dissolving in water using concentrated ammonia as the ammonium salt. Melting point. 79–85° C.

EXAMPLE 2

(3'-deoxy-3'-fluorothymidine)-5'-diphosphoric acid-mono-(3-dodecylmercapto-2-decyloxy)-1-propyl ester The compound was produced analogously to example 1 from the described morpholidate crude product and chromatographically purified 3'-deoxy-3'-fluorothymidine-monophosphate. Yield 47% of theory, paste $R_f$=0.42 (methanol/$H_2O$ 85/15), RP 18 TLC plates Merck.

What is claimed is:
1. A compound of formula I

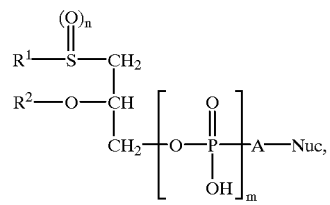

(I)

wherein $R^1$ is a straight-chained or branched, saturated or unsaturated alkyl group containing 9–14 carbon atoms;

$R^2$ is a straight-chained or branched, saturated or unsaturated alkyl group containing 8–12 carbon atoms;

m is 2;

n is 0–2;

A is oxygen; and

Nuc is a coupled nucleoside residue selected from the group consisting of
2',3'-dideoxy-3'-azidouridine,
2',3'-dideoxyinosine,
2',3'-dideoxyguanosine,
2',3'-dideoxycytidine,
2,3'-dideoxyadenosine,
2,3'-deoxthymidine,
2,3'-dideoxy-2'-3'-didehydro-$N^6$-(o-methylbenzyl)-adenosine,
2',3'-dideoxy-2'-3'-didehydro-$N^6$-(2-methylpropyl)-adenosine,
2',3'-dideoxy-3'-azidoguanosine,
3'-deoxy-3'-azido-thymidine,
2',3'-dideoxy-3'-fluoro-5-chlorouridine,
3'-deoxy-3'-fluorothymidine,
2',3'-dideoxy-3'-fluoroadenosine,
2',3'-dideoxy-3'-fluoro-2,6-diaminopurine-riboside,
2',3'-dideoxy-2'-3'-didehydrocytidine,
3'-deoxy-2'-3'-didehydrothymidine,
5-fluorouridine,
6-mercaptopurine-9-β-D-ribofuranoside,
Acyclovir,
Ganciclovir,
adenine-9-β-D-arabinofuranoside,
2-chloro-2'-deoxyadenosine,
3-(2-deoxy-β-D-erythro-pentofuranosyl)-3,6,7,8-tetrahydro-imidazo[4,5-d][1,3]diazepin-8-ol,
cytosine-9-β-D-arabinofuranoside,
guanine-9-β-D-arabinofuranoside,
hypoxanthine-9-β-D-arabinofuranoside,
2'-deoxy-2-fluoroadenosine
2-fluoroadenine-9-β-D-arabinofuranoside,
2-fluoroadenosine,
2-amino-6-mercaptopurine-9-β-D-ribofuranoside,
6-methylmercaptopurine-9-β-D-ribofuranoside,
3'-deoxy-5-fluorouridine,
2-chloroadenosine,
3'-deoxy-3'-fluoroadenosine,
3'-deoxy-3'-fluoroguanosine,
1-(β-D-arabinofuranosyl)-5-ethinyluracil,
1-(β-D-arabinofuranosyl)-5-prop-1-inyluracil, and
1-(β-D-arabinofuranosyl)-5-prop-2-inyluracil, wherein the Nuc moiety is coupled to the moiety A via the 5'-O- position of the sugar residue.

2. The compound of claim 1, wherein Nuc is a coupled 3'-deoxy-3'-azido-thymidine or 3'-deoxy-3'-fluorothymidine residue.

3. The compound of claim 1, wherein Nuc is a coupled 3'-deoxy-3'-azido-thymidine residue.

4. The compound of claim 1, wherein the compound is (3'-deoxy-3'-azido-thymidine)-5'-diphosphoric acid-(3-dodecylmercapto-2-decyloxy)-1-propyl ester or 3'-deoxy-3'-fluorothymidine)-5'-diphosphoric acid-mono-(3-dodecylmercapto-2-decyloxy)-1-propyl ester.

5. A pharmaceutical composition, comprising a compound according to claim 1 and a pharmaceutically acceptable carrier.

6. A method of treating a viral infection in a patient in need thereof, comprising administering to the patient a viral infection-treating or -preventing effective amount of a compound according to claim 1.

* * * * *